United States Patent [19]
Sachetto

[11] Patent Number: 5,972,310
[45] Date of Patent: *Oct. 26, 1999

[54] AQUEOUS FOAMABLE COMPOSITION

[75] Inventor: Jean-Pierre Sachetto, Arlesheim, Switzerland

[73] Assignee: Tillotts Pharma AG, Ziefen, Switzerland

[*] Notice: This patent is subject to a terminal disclaimer.

[21] Appl. No.: 09/086,709

[22] Filed: May 29, 1998

Related U.S. Application Data

[63] Continuation of application No. 08/765,171, Feb. 24, 1997, Pat. No. 5,759,520.

[30] Foreign Application Priority Data

Jul. 21, 1994 [GB] United Kingdom ................... 9414699

[51] Int. Cl.⁶ ..................................................... A61L 9/04
[52] U.S. Cl. ............................. 424/45; 424/47; 424/430; 521/88; 521/92; 521/93
[58] Field of Search ................................ 424/45, 47, 430, 424/DIG. 14, 434; 521/88, 92, 93, 97, 98, 149

[56] References Cited

U.S. PATENT DOCUMENTS

| | | | |
|---|---|---|---|
| 5,171,577 | 12/1992 | Griat et al. | 424/450 |
| 5,352,437 | 10/1994 | Nakagawa et al. | 424/45 |
| 5,369,131 | 11/1994 | Poli et al. | 514/772.4 |
| 5,545,401 | 8/1996 | Shanbrom | 424/78.07 |
| 5,759,520 | 6/1998 | Sachetto | 424/45 |

FOREIGN PATENT DOCUMENTS

| | | |
|---|---|---|
| 395329 | 10/1990 | European Pat. Off. . |
| 468555 | 1/1992 | European Pat. Off. . |
| 2647344 | 11/1990 | France . |
| 91/11991 | 8/1991 | WIPO . |
| 92/01457 | 2/1992 | WIPO . |

OTHER PUBLICATIONS

Hagers Handbuch der Pharmazeutichen Praxis, vol. 2, pp. 623–625 (1991) (with translation).

Primary Examiner—S. Mark Clardy
Assistant Examiner—Kathryne E. Shelborne

[57] ABSTRACT

An aqueous foamable composition is provided having a delayed foaming action on expulsion from a pressurized container. The composition comprises a major amount of water, a water-immiscible liquified gas foaming agent, at least one foam-stabilizing and emulsifying surfactant, and a water-soluble polymer. The composition is particularly useful for rectal or vaginal administration of pharmaceuticals.

68 Claims, No Drawings

AQUEOUS FOAMABLE COMPOSITION

This application is a continuation of application Ser. No. 08/765,171, filed Feb. 24, 1997, now U.S. Pat. No. 5,759,520, issued Jun. 2, 1998.

The present invention relates to an aqueous foamable composition suitable for delivery using known aerosol delivery systems. More particularly, the invention relates to foamable compositions which have a delayed foaming action after delivery, and which are especially suitable for rectal or vaginal delivery of pharmaceutically active ingredients.

It is known to use aqueous foams for rectal administration of pharmaceutical substances. Examples of such foams are disclosed in EP-A-0468555 (Giuliani S.p.A.), EP-A-0395329 (Smith Kline & French) and FR-A-2647344 (Physiopharm). The compositions taught in these prior art documents are so formulated that the same substance or mixture of substances (namely one or more chlorofluorocarbons) is used as both a foaming agent and a propellant for expulsion of the composition out of a conventional aerosol can. These known compositions exhibit immediate foaming on expulsion from the aerosol container.

Intravaginal contraceptive compositions are also known in the art. U.S. Pat. No. 4,588,581 (Schmolka) discloses a liquid contraceptive composition for spraying from a pressurized aerosol container, which is said to form a gel on contact with living tissue. The composition comprises in certain proportions water, propellant, a non-propellant volatile solvent, a sperm function inhibitor and a polyoxyethylene-polyoxybutylene copolymer as a surfactant.

It is an object of the present invention to provide an aqueous foamable composition which exhibits a delayed foaming action on expulsion from a pressurised container. Pharmaceutical compositions exhibiting a delayed foaming action are particularly suitable for rectal or vaginal administration. The two principal advantages associated with a foaming action which is delayed rather than immediate are (1) the likelihood of inducing a defecation or rejection reflex on administration of the composition is much lower; and (2) a better spreading effect is obtained, which leads to increased bioavailability of the active substance.

By "immediate foaming" herein is meant expansion of the foam to its final volume in less than one second following expulsion from the container in question. "Delayed foaming" is obtained when the expansion of the foam to its final volume is achieved after more than one second. Delayed foaming may, however, take place over several minutes. The initial foaming action is partial or negligible.

Non-aqueous foamable compositions with a delayed foaming action are known from WO-A-91/11991 (Kabi Pharmacia). This document teaches the skilled man to exclude water from the compositions with a delayed foaming action. Indeed, it suggests that a delayed foaming action cannot be achieved with aqueous foams. The foamable compositions disclosed in this prior art document contain a liquid polar polyol or polyol mixture as a carrier, particularly polyethylene glycols of low molecular weight (300 to 800). These polyethylene glycols are readily adsorbed and rapidly excreted. However, although they are considered of low toxicity (see Donovan et al, *Pharmaceutical Research* 7(8), 863–868 (1990)), they may contain undesirable residual amounts of monoethylene glycol, diethylene glycol and ethylene oxide. Water is advantageous since it is a safer vehicle, and is also much less expensive. The other essential components of the non-aqueous foamable compositions disclosed in WO-A-91/11991 are at least one foam-stabilizing and emulsifying surfactant, a pharmaceutically active ingredient and a suitable propellant.

We have surprisingly found that by employing an appropriate combination of materials it is possible to produce an aqueous foamable composition having a delayed foaming action.

According to one aspect of the invention, we therefore provide an aqueous foamable composition having a delayed foaming action on expulsion from a pressurised container, the composition comprising:

(a) a major amount by weight of water;
(b) 0.5 to 7.0 weight percent of a foaming agent in the form of a water-immiscible liquefied gas;
(c) at least one foam-stabilising and emulsifying surfactant; and
(d) a water-soluble polymer.

As mentioned above, this composition is of particular use for rectal or vaginal administration of pharmaceuticals. For medical use, the composition will also contain a pharmaceutically active ingredient. If desired, a muco-adhesive ingredient may also be included. Conventional additives for pharmaceutical compositions are optionally also present.

The aqueous foamable compositions of the present invention exhibit significant advantages over the known non-aqueous compositions having a delayed foaming action. Firstly, when used for rectal or vaginal administration of pharmaceuticals, an aqueous foam permits one to use in the compositions muco-adhesive polymers, which are usually water-soluble or water-dispersible. These muco-adhesive polymers can substantially increase rectal/vaginal retention time, so leading to increased topical action of the foam and hence of the drug, and increasing bioavailability of the pharmaceutical. Examples of such muco-adhesive polymers are carboxymethylcellulose and carbomers. It is noteworthy that the muco-adhesive force of polyethylene glycol (used in the known compositions disclosed in WO-A-91/11991) is much lower. Furthermore, neither carboxymethylcellulose or carbomer is soluble in polyethylene glycols; in fact, carbomer reacts with polyethylene glycols to give hard, tough complexes.

In addition, the manufacturing process is simpler for aqueous foamable compositions, since the mixture of the vehicle and surfactant does not need to be heated and subsequently cooled, as it does in the preparation of non-aqueous foamable compositions exhibiting a delayed foaming action.

In the foamable compositions of the invention, water is the vehicle for the other components. The compositions of the invention comprise preferably 57–97 weight percent of water, more preferably 65–95 weight percent. The presence of another polar liquid (i.e. a water-soluble or water-miscible liquid mixture of polar liquids) in admixture with the water is acceptable provided that the desired foaming properties of the compositions are not destroyed. Examples of polar liquids which can be mixed with the water are glycerol, propylene glycol and polyethylene glycols.

The foaming agent of the composition is preferably a so-called liquefied gas, i.e. a gas which can be liquefied at a relatively low pressure at ambient temperature. Suitable foaming agents are propane, butane, iso-butane, pentane and mixtures of these alkanes. These foaming agents are immiscible with water and are liquefied when pressurised in the compositions of the invention. As may be seen from Table I, they also have a relatively high boiling point and a relatively low vapour pressure compared with other gases commonly used as foaming agents, e.g. oxygen, nitrogen, carbon dioxide and nitrous oxide. For environmental reasons, it is preferred not to use chlorofluorocarbons as foaming agents. However, more recently developed environmentally friendly propellants such as 1,1,1,2-tetrafluoroethane (134a/P) and 1,1,1,2,3,3,3-heptafluoropropane (HFA 227) are suitable for use as foaming agents in the present invention.

TABLE I

| Foaming agent | Vapour pressure at 21° C. (kpa) | Boiling point (°C.) |
|---|---|---|
| propane | 855 | −43.0 |
| iso-butane | 317 | −12.7 |
| butane | 221 | −0.5 |
| pentane | 56 | +36.1 |
| 134a/P | 590 | −26.0 |
| HFA 227 | 403 | −16.0 |

The compositions of the invention contain 0.5 to 7.0 weight percent of foaming agent, preferably 1.0 to 3.5 weight percent.

The surfactant or mixture of surfactants incorporated in the compositions of the invention can be chosen from those which have an effective emulsifying action in relation to water and the foaming agent. Preferred are anionic and non-ionic surfactants, e.g. polyoxyethylene sorbitan esters, polyoxyethylene fatty esters, alkyl phenoxy ethanols, fatty acid esters, alkanolamides and alkyl sulphates such as sodium lauryl sulphate. Most preferred are polyoxyethylene sorbitan esters which are liquid non-ionic surfactants, e.g. Polysorbate 80 (polyoxyethylene 20 sorbitan monooleate, CAS 9005-65-6) and Polysorbate 20 (polyoxyethylene 20 sorbitan monolaurate, CAS-9005-64-5).

The compositions of the invention typically contain up to 3 weight percent of surfactant, preferably 0.1 to 2 weight percent.

The precise identity of the water-soluble polymer in the compositions of the invention is not critical, but we have found that water-soluble polysaccharides having none or very few polar groups (such as carboxylates, sulphates and phosphates) are suitable. The water-soluble polymers are preferably selected from xanthan gum, agar, guar gum, hydroxyethyl cellulose, hydroxypropyl cellulose, hydroxypropyl methylcellulose and methyl cellulose. Xanthan gum is most preferred.

The compositions of the invention typically contain up to 5 weight percent of water-soluble polymer, preferably 0.1 to 3 weight percent.

As mentioned above, the compositions of the invention may be used to deliver pharmaceutically active ingredients. Since the compositions are aqueous, such active ingredients should be insensitive to water.

According to another aspect of the invention, we therefore provide an aqueous foamable pharmaceutical composition having a delayed foaming action on expulsion from a pressurised container, the composition comprising the following pharmaceutically acceptable components:

(a) a major amount by weight of water,
(b) 0.5 to 7.0 weight precent of a foaming agent in the form of a water-immiscible liquefied gas;
(c) at least one foam-stabilising and emulsifying surfactant;
(d) a water-soluble polymer;
(e) an effective amount of active substance; and
(f) if desired, a muco-adhesive agent and/or one or more conventional pharmaceutical additives.

According to a further aspect of the invention, there is provided a composition of the invention as defined hereinbefore for use in therapy.

The compositions of the invention are especially suitable for rectal or vaginal administration of pharmaceutically active substances.

Examples of clinical conditions which can benefit from treatment by rectal administration of pharmaceutical substances are constipation, bowel evacuation, inflammatory bowel diseases (ulcerative colitis, Crohn's disease), irritable bowel syndrome and anorectal disorders. Unwanted gastrointestinal side effects, for example those which might be caused by administering analgesics to children, may also be prevented by rectal administration of suitable pharmaceuticals.

According to a still further aspect of the invention, there is provided a method of treatment of conditions of the colon or lower gastrointestinal tract of the human or animal body, comprising rectal administration of a pharmaceutical composition of the invention as defined hereinbefore.

Examples of clinical conditions which can benefit from treatment/prophylaxis by vaginal administration of pharmaceutical substances are sexually transmitted diseases (STD's), i.e. the sexual transmission of fungal, protozoal, bacterial and viral diseases. The invention can also be employed as a contraceptive, by using spermicides as a component of the foamable composition.

According to a still further aspect of the invention, there is provided a method of combating the transmission of sexually transmitted diseases comprising the vaginal administration of a pharmaceutical composition of the invention as defined hereinbefore.

The delayed foaming effect shown by compositions of the invention gives rise to a better spreading effect than can be obtained with known aqueous foamable compositions. This is particularly important in the treatment of distally localised colonic diseases or for intravaginal use to prevent STD's.

According to a yet further aspect of the invention, there is provided the use of a composition of the invention for the manufacture of a medicament for combating diseases of the colon or lower gastro-intestinal tract.

According to a yet further aspect of the invention, there is provided the use of a composition of the invention for the manufacture of a medicament for combating the sexual transmission of fungal, protozoal, bacterial and viral diseases.

Some active substances must be delivered rectally, either because they act directly on the colon, or because they are metabolised in the liver or decompose as a result of the acidity of gastric juice or by the action of gastro-intestinal enzymes. Other active substances are advantageously administered rectally. Among active ingredients for treating gastro-intestinal conditions which may be mentioned by way of example only are: a water-soluble complex of bismuth and a polyacrylate, e.g. a bismuth-carbomer complex (as described in WO-A-92/01457); laxatives, e.g. bulk laxatives such as methylcellulose and psyllium, stimulant laxatives such as $Na^+/K^+$ ATPase blocker, Ricin oil, anthraquinone, bisacodyl and $Na^+$ picosulphate, or osmotic laxatives such as magnesium sulphate, magnesium citrate, lactulose, lactose and sorbitol; antidiarrhoeal agents, e.g. codeine, diphenoxylate and loperamide; anti-inflammatory agents, e.g. 4- and 5-aminosalicylic acid (known as 4-ASA and 5-ASA), prednisolone sodium metasulphobenzoate, hydrocortisone, budesonide, cyclosporine, beclomethasone dipropionate, fish oils, azathioprine and 6-mercaptopurine; local and synergistic analgesics, e.g. morphine; and substances for systemic effect, such as insulin, peptides and enzymes, which are metabolised to a great extent at first bypass in the liver or which are decomposed by the gastro-intestinal enzymes.

Among active ingredients for the prophylactic treatment of STD's which may be mentioned by way of example only are: polysulphated polysaccharides including carrageenans and modified heparin without anti-coagulant activity, which have been shown to block herpes virus and HIV infections in vitro; bile acid derivatives, which have displayed activity against enveloped viruses and chlamydia; spermicides such as nonoxyl-9 (which has been associated with decreased transmission of HIV when used in moderate amounts) and benzalkonium chloride; methyl esters of short-chain fatty acids, which disrupt the membranes of gram-negative bacteria and enveloped viruses; peptide antibiotics such as defensins and protegrins, which are known to attack enveloped viruses as well as protozoa and bacteria; and haloperoxidase, which is known to selectively inhibit pathogenic microbes present in sexually transmitted fluids.

The precise amount of active ingredient used will depend upon inter alia the identity of the active ingredient and the condition against which it is directed. Generally, however, the active ingredient will comprise from 0.001 to 25 weight percent of the composition.

When it is desired to include a muco-adhesive ingredient in the compositions of the invention, known muco-adhesive polymers such as sodium carboxymethyl-cellulose, poly (acrylic acid) such as carbomer, tragacanth, poly(ethylene oxide), sodium alginate, soluble starch, gelatin, pectin, poly (vinyl pyrrolidone), poly(ethylene glycol) and poly(vinyl alcohol) are suitable. The preferred muco-adhesive is carbomer, e.g. that is available under the name Carbopol 934P.

The amount of muco-adhesive agent which may be used in the compositions of the invention is typically up to 3 weight percent, preferably 0.1 to 1.5 weight percent.

Other additives which may optionally also be present in the compositions of the invention include those additives conventionally employed in pharmaceutical compositions or in foam formulations, for example suspending agents, dispersing agents, antioxidants, preservatives and foam-stiffening agents. These are typically present in an amount of up to 5 weight percent of the composition, preferably 0 to 2 weight percent.

The manufacture of the foamable compositions of the invention is carried out according to the usual techniques used to manufacture formulations to be introduced into pressurised containers. By way of example only, manufacture may be carried out as follows.

The water-soluble polymer is firstly dispersed in the water by means of a high speed homogeniser. The muco-adhesive agent, if required, is also then dispersed in the same way. The optional additives (e.g. foam-stiffening agents, suspending agents, dispersing agents, antioxidants, preservatives) can be added at this stage. The pH of the dispersion may then be adjusted to the desired value using a suitable acid or alkali. For pharmaceutical use, a neutral pH of around 7.0±0.2 is required. Thus, for example, if the pH of the dispersion resulting from the foregoing process steps is too low, neutralisation may be carried out by using a 10% (by weight) aqueous NaOH solution. In some cases, an acid or alkaline pH is required for efficacy of the active ingredient, or to lower its systemic absorption. For example, 5-ASA requires a pH of 4 to 5.

The pharmaceutically active ingredient and the surfactant may then also be dispersed in the mixture. The concentrate thus obtained is then transferred into a pressurised mixing tank, where it is blended with the foaming agent. The resulting blend is transferred to a dosing and filling tank, from where it is used to fill the final packaging, e.g. a pressurised aerosol canister.

Three types of aerosol containers are known for rectal application of foams, and are suitable for use in conjunction with the present invention. The three types of container are the conventional "monobloc" system; the "bag-in-can" system and the "can with piston" system. These generally require the use of a propellant gas. In connection with the present invention, a "bag-in-can" or "can with piston" system requires a separate propellant. For a monobloc system, the addition of a small amount of propellant in the can with the foamable composition is recommended. Nitrogen is a suitable propellant. The weight of propellant added is generally between 2 and 10% of the weight of the composition, e.g. for 20 g of the composition, between 0.4 g and 2 g of nitrogen may be added to the aerosol can.

A further aspect of the invention is provided by an article for dispensing a pharmaceutical composition of the invention, comprising a pressurised aerosol container containing said pharmaceutical composition and, optionally, a propellant.

The ingredients of the compositions discussed above are all pharmaceutically acceptable. As mentioned, the components are mixed in proportions such that a delayed foaming action is obtained, i.e. a stream of liquid is initially released from the aerosol container which liquid is capable of flowing readily at first but then expands at a controlled rate to form a foam, the rate of expansion depending upon the proportions of the basic components (a), (b), (c) and (d) defined above. In preferred compositions of the invention, the final volume of the foam is 10 to 20 times the volume of the initial liquid, i.e. the composition has an expansion ratio of 10 to 20.

For a better understanding of the invention, the following non-limiting Examples are set forth. For a number of different formulations, a variety of different properties were investigated: the rate of foaming; the initial volume of (liquid) composition; the final volume of foam; the expansion ratio; and the time required for expansion of the composition to 50% of the final foam volume. All these properties were measured at 37° C. n-Butane was used as the foaming agent. The foaming rate was determined by delivering the foamable composition into a graduated cylinder pre-warmed and maintained at 37° C. The foaming rate is defined as the ratio between 50% of the final foam volume (in ml) and the time (in seconds) required for the composition to reach said 50% volume after expulsion from the container. The units of foaming rate are therefore ml/sec. The initial volume of the foamable compositions can be determined from the weight thereof divided by its density at 37° C. (Generally, the density of the formulations is close to unity.) The expansion ratio is defined as the ratio between the final volume of the foam and the initial volume of the corresponding foamable composition. Viscosities were measured by means of a Brookfield Viscometer Model DV-II, using spindle 64 at 1.5 rpm and 20° C.

EXAMPLE 1

2 g of xanthan gum (water-soluble polymer) were dispersed in 98 g of water. 1 g of Polysorbate 80 (surfactant) was then dispersed in the viscous mixture. In a pressurised tank, 2.5 g of n-butane were blended with the dispersion, and the resulting blend was introduced into a pressurised canister (bag-in-can).

Upon release of the foamable composition from the canister, a white foam was obtained which had a foaming rate of 5.2 ml/sec. 22.5 g of the formulation ultimately gave 290 ml of foam at 37° C. The expansion ratio was therefore 12.9. 50% of the final foam volume was attained after 28 seconds.

For the purposes of comparison, five other compositions were made in accordance with the above example, but omitting one of the components. The water-soluble polymer was excluded from comparative formulation A; the foaming agent (liquefied gas) was excluded from comparative formulation B; in comparative formulation C the liquefied gas was replaced by a chloroflurocarbon gas, and in comparative formulation D by nitrogen (a non-liquefied gas); and in comparative formulation E, the surfactant was excluded.

Comparative formulation A gave an immediate liquefied foam which had no strength. Comparative formulations C and D also gave immediate foams. Comparative formulations B and E did not give rise to a foam at all. This illustrates that all of the components (a) to (d) as defined herein are essential for the delayed foaming action of the compositions of the invention.

EXAMPLE 2

A pharmaceutical composition was formulated with prednisolone sodium metasulphobenzoate as active pharmaceutical ingredient, in accordance with the data shown in Table II below. The basic formulation in accordance with Example 1 is also shown for comparison.

TABLE II

| | Basic formulation of Ex. 1 | | Active formulation | |
|---|---|---|---|---|
| | weight (g) | % w/w | weight (g) | % w/w |
| $H_2O$ | 98.0 | 94.70 | 93.85 | 90.70 |
| Xanthan gum | 2.0 | 1.90 | 2.0 | 1.90 |
| Polysorbate 80 | 1.0 | 0.95 | 1.0 | 0.95 |
| Preservatives | — | | 0.17 | 0.16 |
| Soya lecithin | — | | 0.20 | 0.19 |
| Carbopol 974P | — | | 0.60 | 0.58 |
| NaOH (10%) | — | | 2.55 | 2.40 |
| Prednisolone sodium meta-sulphobenzoate | — | | 0.625 | 0.60 |
| n-butane | 2.5 | 2.40 | 2.5 | 2.40 |
| Total | 103.5 | 100.00 | 103.5 | 100.00 |

The active formulation was used to fill a bag-in-can canister. When released from the can, it gave a white foam with an expansion rate of 5 ml/sec at 37° C. 22 g of the formulation gave 275 ml of foam. The expansion ratio was therefore 12.5. 50% of the final foam volume was attained after 27 seconds. This Example shows that the basic components (a) to (d) exercise a dominant influence on the foaming behaviour of pharmaceutical foamable compositions of the invention.

EXAMPLES 3 to 8

Six compositions were formulated to investigate the influence of the proportion and type of water-soluble polymer on the delayed foaming properties of the compositions. The formulations are shown in Table III below. Examples 3 to 5 contained xanthan gum as the water-soluble polymer, whereas Examples 6 to 8 contained carbomer.

As can be seen from Examples 3 to 5, the rate of foaming is the same between 1% and 2% of the xanthan gum (at a viscosity of 23,000 to 49,000 centipoise). At 3% by weight (and 97,000 cps) the foaming rate is significantly decreased. A xanthan gum concentration of around 2% by weight appears to be optimal, since it gives a delayed foaming action (5.2 ml/sec foaming rate) in combination with a relatively large expansion ratio (12.9). If a slow foaming rate is required, the concentration of xanthan gum may be increased above 2% by weight. However, we would expect the foaming rate to be very slow above 3% by weight.

It can be seen from Examples 6 to 8 that the foaming rate is the same at 0.4 and 0.6 weight percent of carbomer (at which concentrations the viscosity is 130,000 and 180,000 cps respectively). At 0.2 weight percent concentration, the foaming rate is increased slightly from 18.7 ml/sec to 25 ml/sec. A concentration of 0.2 weight percent may be preferred, since it gives the highest expansion ratio of these three Examples.

Xanthan gum may be classified as a "neutral" water-soluble polymer, whilst carbomer is a "polyelectrolyte" water-soluble polymer. At the similar viscosities of the compositions of Examples 5 and 8, it can be seen that the former (with one weight percent xanthan gum) exhibits a slower foaming rate than the latter (containing 0.2 weight percent carbomer). The xanthan gum therefore appears more effectively to delay the foaming action.

TABLE III

| | Ex. 3 | Ex. 4 | Ex. 5 | Ex. 6 | Ex. 7 | Ex. 8 |
|---|---|---|---|---|---|---|
| | Composition (% wt. content) | | | | | |
| Xanthan gum | 3 | 2 | 1 | — | — | — |
| Carbomer (sodium salt) | — | — | — | 0.6 | 0.4 | 0.2 |
| Surfactant (Polysorbate 80) | 1 | 1 | 1 | 1 | 1 | 1 |
| Foaming agent | 2.5 | 2.5 | 2.5 | 2.5 | 2.5 | 2.5 |
| $H_2O$ | 93.5 | 94.5 | 95.5 | 95.9 | 96.1 | 96.3 |
| Viscosity (cps) | $97 \times 10^3$ | $49 \times 10^3$ | $23 \times 10^3$ | $180 \times 10^3$ | $130 \times 10^3$ | $28 \times 10^3$ |
| Rate of foaming (ml/sec) | 1.4 | 5.2 | 5.2 | 18.7 | 18.7 | 25.0 |
| Expansion ratio | 9.4 | 12.9 | 9.6 | 10.0 | 10.0 | 10.7 |
| Time taken to reach 50% of final foam volume (sec) | 72 | 28 | 22 | 6 | 5.3 | 4.7 |

EXAMPLES 9 TO 14

These Examples are intended to illustrate the effect of varying the surfactant concentration of compositions of the invention. Polysorbate 80 is the surfactant used in these Examples. Examples 9 to 11 employ xanthan gum as the water-soluble polymer, whilst Examples 12 to 14 employ carbomer (sodium salt). The compositions and properties of the Examples are shown in Table IV below.

It can be seen from Examples 9 to 11 that the foaming rate of a basic formulation can be reduced by decreasing the surfactant content. The expansion ratio also decreases somewhat, although the expansion ratio of around 10 in the range of 1 to 2 weight percent xanthan gum is an acceptable one.

When carbomer is used as the water-soluble polymer, decreasing the surfactant content has a relatively smaller influence on the foaming rate, as can be seen from Examples 12 to 14. Also, the expansion ratio exhibits only a small variation in the range of 0.5 to 3 weight percent surfactant. Accordingly, a level of around 0.5 weight percent surfactant will generally be preferred in such a formulation, for reasons of cost.

TABLE IV

|  | Ex. 9 | Ex. 10 | Ex. 11 | Ex. 12 | Ex. 13 | Ex. 14 |
|---|---|---|---|---|---|---|
|  | Composition (% wt. content) | | | | | |
| Xanthan gum | 3 | 3 | 3 | — | — | — |
| Carbomer (sodium salt) | — | — | — | 0.6 | 0.6 | 0.6 |
| Surfactant | 2 | 1 | 0.5 | 2 | 1 | 0.5 |
| Foaming agent | 2.5 | 2.5 | 2.5 | 2.5 | 2.5 | 2.5 |
| $H_2O$ | 92.5 | 93.5 | 94 | 94.9 | 95.9 | 96.4 |
| Viscosity (cps) | $97 \times 10^3$ | $97 \times 10^3$ | $97 \times 10^3$ | $180 \times 10^3$ | $180 \times 10^3$ | $180 \times 10^3$ |
| Rate of foaming (ml/sec) | 3.8 | 1.4 | 1.1 | 18.7 | 18.7 | 12.5 |
| Expansion ratio | 11 | 9.4 | 8.5 | 9.7 | 10 | 10 |
| Time taken to reach 50% of final foam volume (sec) | 35 | 72 | 75 | 6 | 6 | 5 |

EXAMPLES 15 TO 20

Six compositions were formulated in order to investigate the influence of the amount of foaming agent on the foaming properties of the composition, using either xanthan gum or carbomer (sodium salt) as the water-soluble polymer. The compositions and properties of these Examples are shown in Table V below.

It can be seen from Examples 15 to 17 that decreasing the amount of foaming agent from 3.5 to 1.5 weight percent decreases the foaming rate and the expansion ratio. Examples 18 to 20 show a corresponding trend. Using either 3 weight percent of xanthan gum or 0.6 weight percent of carbomer (sodium salt) as the water-soluble polymer, a foaming agent content of 2.5 to 3.5 weight percent is seen to give a satisfactory expansion ratio for the compositions.

TABLE V

|  | Ex. 15 | Ex. 16 | Ex. 17 | Ex. 18 | Ex. 19 | Ex. 20 |
|---|---|---|---|---|---|---|
|  | Composition (% wt. content) | | | | | |
| Xanthan gum | 3 | 3 | 3 | — | — | — |
| Carbomer (sodium salt) | — | — | — | 0.6 | 0.6 | 0.6 |
| Surfactant (Polysorbate 80) | 1 | 1 | 1 | 1 | 1 | 1 |
| Foaming agent | 3.5 | 2.5 | 1.5 | 3.5 | 2.5 | 1.5 |
| $H_2O$ | 92.5 | 93.5 | 94.5 | 94.9 | 95.9 | 96.9 |
| Viscosity (cps) | $97 \times 10^3$ | $97 \times 10^3$ | $97 \times 10^3$ | $180 \times 10^3$ | $180 \times 10^3$ | $180 \times 10^3$ |
| Rate of foaming (ml/sec) | 4.3 | 1.4 | 0.6 | 30 | 18.7 | 2 |
| Expansion ratio | 14 | 9.4 | 6.7 | 14.3 | 10 | 5.5 |
| Time taken to reach 50% of final foam volume (sec) | 41 | 72 | 125 | 5 | 6.4 | 26.5 |

EXAMPLE 21

In this Example, xanthan gum and carbomer (sodium salt) were used in combination as the water-soluble polymer. Details of the formulation are shown in Table VI below, together with details of Examples 5 and 8 for comparison.

TABLE VI

|  | Ex. 5 Composition | Ex. 8 | Ex. 21 (blend) (% wt. content) |
|---|---|---|---|
| Xanthan gum | 1 | — | 1 |
| Carbomer (sodium salt) | — | 0.2 | 0.2 |
| Surfactant (Polysorbate 80) | 1 | 1 | 1 |
| Foaming agent | 2.5 | 2.5 | 2.5 |
| $H_2O$ | 95.5 | 96.3 | 95.3 |
| Viscosity (cps) | $23 \times 10^3$ | $28 \times 10^3$ | $28 \times 10^3$ |
| Rate of foaming (ml/sec) | 5.2 | 25 | 5.8 |
| Expansion ratio | 9.6 | 10.7 | 9.9 |
| Time taken to reach 50% of the final foam volume (sec) | 22 | 4.7 | 17.4 |

As noted above in relation to Examples 3 to 8, xanthan gum produces a more pronounced detailed foaming effect than carbomer. When the two polymers are blended, the viscosity remains essentially unchanged, but the more pronounced delayed foaming effect of xanthan gum is maintained in the blend. As can be seen from Table VI, the expansion ratio of the three Examples is very similar, but the foaming rate of Example 21, which contains the polymer blend, is similar to that of Example 5. By contrast, the composition of Example 8, which has similar viscosity and expansion ratios to the other two blends, shows a foaming rate nearly five times higher.

As noted hereinbefore, the carbomer may also act as a muco-adhesive. Accordingly, when a foamable composition of the invention contains carbomer as muco-adhesive, the presence of appropriate amounts of xanthan gum allows one to adjust the foaming rate as desired. This can also be seen from Example 2 above.

EXAMPLES 22 TO 25

Four compositions were formulated in order to investigate the effect of varying the nature and quantity of surfactant. Details of the compositions and their properties are given in Table VII below. Sodium lauryl sulphate is an anionic surfactant, and Polysorbate 80 is a non-ionic surfactant.

At a 2% by weight content, the two types of surfactant have an equivalent effect, the anionic surfactant leading a slightly slower foaming rate (Example 22). When the level of ionic sodium lauryl sulphate is reduced from 2 to 0.5 weight percent, the foaming rate decreases but the expansion ratio is similar Example 24). A corresponding trend is shown as between Examples 23 and 25.

When a 50:50 blend of anionic and non-ionic surfactants is used (Example 25), the foaming rate is found to be slightly higher than the foaming rate of a composition containing 1% by weight of only non-ionic surfactant (Example 5). However, using the aforesaid blend, the expansion ratio is significantly higher than the expansion ratio of the composition of Example 5. Accordingly, an anionic surfactant may be used instead of a non-ionic surfactant in compositions of the invention. Anionic surfactants are widely used in known foam formulations, although non-ionic surfactants are often preferred because, being uncharged, they may be less likely to be incompatible with other components.

TABLE VII

|  | Ex. 22 | Ex. 23 | Ex. 24 | Ex. 25 | Ex. 5 |
|---|---|---|---|---|---|
|  | Composition (% wt. content) | | | | |
| Xanthan gum | 1 | 1 | 1 | 1 | 1 |
| Sodium lauryl sulphate | 2 | — | 0.5 | 0.5 | — |
| Polysorbate 80 | — | 2 | — | 0.5 | 1 |
| Foaming agent | 2.5 | 2.5 | 2.5 | 2.5 | 2.5 |

TABLE VII-continued

|  | Ex. 22 | Ex. 23 | Ex. 24 | Ex. 25 | Ex. 5 |
|---|---|---|---|---|---|
|  | Composition (% wt. content) | | | | |
| H$_2$O | 94.5 | 94.5 | 96.0 | 95.5 | 95.5 |
| Viscosity (cps) | 23 × 10$^3$ | 23 × 10$^3$ | 23 × 10$^3$ | 23 × 10$^3$ | 23 × 10$^3$ |
| Rate of foaming (ml/sec) | 9.5 | 10.0 | 5.0 | 7.0 | 5.2 |
| Expansion ratio | 11.6 | 11.5 | 11.6 | 11.3 | 9.6 |
| Time taken to reach 50% of the final volume (sec) | 13.0 | 11.5 | 25.0 | 17.0 | 22.0 |

EXAMPLE 26

A composition was formulated which had a relatively low viscosity. Details of the composition and its properties are given below.

|  | Ex. 26 |
|---|---|
|  | Composition (% wt. content) |
| Xanthan gum | 0.5 |
| Polysorbate 80 | 1.0 |
| n-butane | 2.5 |
| H$_2$O | 96.0 |
| Viscosity (cps) | 10 × 10$^3$ |
| Rate of foaming (ml/sec) | 13.6 |
| Expansion ratio | 10.9 |
| Time taken to reach 50% of final foam volume (sec) | 10 |

This Example illustrates that a delayed foaming action may be obtained even with compositions having relatively low viscosity.

EXAMPLE 27

The compositions of Examples 1 to 26 all give rise to foams having a satisfactory degree of stiffness, i.e. the foams coalesce only after a couple of hours at 37° C. However, in some circumstances it may be desirable to produce a stiffer foam. Accordingly, a composition was formulated which included a stiffening agent.

|  | Ex. 27 |
|---|---|
|  | Composition (% wt. content) |
| Xanthan gum | 0.5 |
| Polysorbate 80 | 1.0 |
| n-butane | 3.0 |
| emulsifying wax (stiffening agent) | 0.5 |
| H$_2$O | 96.0 |
| Viscosity (cps) | 10 × 10$^3$ |
| Rate of foaming (ml/sec) | 25 |
| Expansion ratio | 13 |
| Time taken to reach 50% of final foam volume (sec) | 6 |

The foam produced by this composition does not coalesce even after ten hours or more at 37° C.

EXAMPLE 28

The compositions of the Examples 1 to 27 are all formulations for hydrophilic foams. It may happen that some pharmaceutically active ingredients are more easily dispersed in a hydrophobic formulation. An Example of such a formulation having a delayed foaming action is given hereafter.

|  | Ex. 28 |
|---|---|
|  | Composition (% wt content) |
| Xanthan gum | 0.2 |
| Carbomer (sodium salt) | 0.5 |
| Hard Fat NF (hydrophobing agent) | 4.5 |
| Emulsifying wax | 2.0 |
| Polysorbate 80 | 1.0 |
| n-butane | 2.0 |
| H$_2$O | 89.8 |
| Viscosity (cps) | 41 × 10$^3$ |
| Rate of foaming (ml/sec) | 5.0 |
| Expansion ratio | 8.0 |
| Time taken to reach 50% of final foam volume (sec) | 20.0 |

EXAMPLES 29 (Comparative) AND 30

These Examples illustrate the comparative in vitro behaviour of a formulation having a delayed foaming action with one having an instantaneous foaming action. For this purpose a model colon was used.

The model colon was constructed using an extended soft dialysis tubing of 29 mm in diameter and 1 m in length placed inside a transparent plastic sheathing of 80 mm in diameter and 1 m in length.

The whole system was immersed in a water-bath at 37° C. The dialysis tubing was attached at one end to the plastic sheathing through a circular plastic adapter and both were connected tightly to an opening in the wall of the water bath. The opening bore a plastic tap allowing the system to be closed to the surroundings after application of the foamable composition. The other end of the dialysis tubing was also attached to the plastic sheathing through a circular plastic adapter and then connected to the atmosphere by means of a flexible pipe. Water was circulated gently (by means of a small circulating pump) between the soft flexible dialysis tubing (representing the colon) and the plastic sheathing thereby simulating the peristaltic movements of the colon. The foamable formulations were applied to the dialysis tubing through its inlet connected to the opening in the wall of the water-bath.

The extent of spreading of the foam within the dialysis tubing was measured at different periods of time. The spreading of various foams in this model colon was found to corrrelate well with the in vivo spreading of the same foam formulations in volunteers as determined by gamma scintigraphy.

The formulations of Examples 29 and 30 were as follows:

|  | Ex. 29 Composition | Ex. 30 (% wt content) |
|---|---|---|
| Xanthan gum | — | 3 |
| Carbomer (sodium salt) | 0.2 | — |
| Emulsifying wax | 0.5 | 0.5 |
| Surfactant (Polysorbate 20) | 2.0 | 2.0 |
| Foaming agent | 2.5 (CFC's) | 2.5 (n-butane) |
| H$_2$O | 94.8 | 92.0 |
| Viscosity (cps) | 30 × 10$^3$ | 100 × 10$^3$ |
| Rate of foaming | instant | 1.4 ml/sec |
| Expansion ratio | 10.0 | 10.0 |

23 g of each of the above foam formulations were applied to the model colon, in both cases corresponding to 230 ml of foam volume as measured by the graduated cylinder method at 37° C., described on page 10 hereinabove.

With the formulation of Example 29, an instant foam was obtained, the dialysis tubing being filled over a length of 35 cm immediately. The foam finally spread up to a length of 48 cm after 90 minutes and did not spread further.

With the formulation of Example 30, only a length of 10 cm of the dialysis tubing was filled initially by the formulation (appearing as a gel). The gel started to foam and the foam expanded slowly to a length of 35 cm of the tubing (reached 8 minutes after the application). The foam continued to spread further and reached 55 cm along the length of the dialysis tubing after 90 minutes.

These two Examples illustrate the benefit of the delayed foaming action over the instant foaming action in that the former occupies a smaller volume initially as a gel, expands slowly to a foam which then occupies the same volume as the corresponding "instant" foam but then spreads further than the latter does.

I claim:

1. A product for rectal or vaginal administration, said product comprising a pressurized bag-in-can container containing an aqueous foamable composition having a delayed foaming action on expulsion from said pressurised container and a propellant separate therefrom for expelling said composition from the container, said composition comprising:
   (a) a major amount by weight of water;
   (b) a foaming agent in the form of a water-immiscible liquefied gas;
   (c) at least one emulsifying surfactant; and
   (d) a water-soluble polymer.

2. A product for rectal or vaginal administration, said product comprising a pressurised container containing an aqueous foamable composition having a delayed foaming action on expulsion from said pressurised container and a propellant separate therefrom for expelling said composition from the container, said composition comprising:
   (a) a major amount by weight of water;
   (b) a foaming agent in the form of a water-immiscible liquefied gas;
   (c) at least one emulsifying surfactant;
   (d) a water-soluble polymer; and
   (e) an effective amount of a pharmaceutically active water-soluble complex of bismuth and a polyacrylate.

3. A product as claimed in claim 2, wherein the pressurised container is a bag-in-can container.

4. A product as claimed in claim 2, wherein the pressurised container is a piston with can container.

5. A product as claimed in claim 2, wherein said composition comprises 57 to 97 weight percent of water.

6. A product as claimed in claim 5, wherein said composition comprises 65 to 95 weight percent of water.

7. A product as claimed in claim 1, comprising 0.5 to 7.0 weight percent of foaming agent.

8. A product as claimed in claim 7, comprising 1.0 to 3.5 weight percent of foaming agent.

9. A product as claimed in claim 7, wherein the foaming agent is selected
   from the group consisting of propane, butane, iso-butane, pentane, 1,1,1,2-tetrafluoroethane, 1,1,1,2,3,3,3,-heptafluoropropane, and mixtures thereof.

10. A product as claimed in claim 1, comprising 0.1 to 2 weight percent of emulsifying surfactant.

11. A product as claimed in claim 10, wherein the emulsifying surfactant is selected from the group consisting of polyoxyethylene sorbitan esters, polyoxyethylene fatty esters, alkyl phenoxy ethanols, fatty acid esters, alkanoamides and alkyl sulphates.

12. A product as claimed in claim 11, wherein said emulsifying surfactant is a polyoxyethylene sorbitan ester.

13. A product as claimed in claim 1, comprising 0.1 to 3 weight percent water-soluble polymer.

14. A product as claimed in claim 13, wherein the water-soluble polymer is a water-soluble polysaccharide.

15. A product as claimed in claim 14, wherein the polysaccharide is selected from the group consisting of xanthan gum, agar, guar gum, hydroxyethyl cellulose, hydroxypropyl cellulose, hydroxypropyl methylcellulose and methyl cellulose.

16. A product as claimed in claim 15, wherein the water-soluble polymer is xanthan gum at 1 to 3% w/w.

17. A product as claim in claim 1, wherein the composition further comprises an effective amount of a pharmaceutically active substance.

18. A product as claimed in claim 17, wherein the active substance is present in an amount of 0.001 to 25 weight percent of the composition.

19. A product as claimed in claim 2, wherein the active substance is a water soluble bismuth-carbomer complex.

20. A product as claimed in claim 17, wherein a mucoadhesive agent is present in an amount of 0.1 to 1.5 weight percent.

21. A product as claimed in claim 20, wherein the mucoadhesive agent is selected from the group consisting of sodium carboxymethylcellulose, polyacrylic acid, tragacanth, polyethylene oxide, sodium alginate, soluble starch, gelatin, pectin, polyvinyl pyrrolidone, polyethylene gylcol and polyvinyl alcohol.

22. A product as claimed in claim 21, wherein the mucoadhesive agent is carbomer.

23. A product composition as claimed in claim 1, having an expansion ratio of 10 to 20.

24. A product for rectal or vaginal administration, said product comprising a pressurised bag-in-can container containing an aqueous foamable composition having a delayed foaming action on expulsion from said pressurised container and a propellant separate therefrom for expelling said composition from the container, said composition comprising:
   (a) 65 to 95 weight percent of water;
   (b) 1.0 to 3.5 weight percent of foaming agent selected from the group consisting of propane, butane, isobutane, pentane, 1,1,1,2-tetrafluoroethane, 1,1,1,2,3,3, 3-heptafluoropropane, and mixtures thereof;
   (c) 0.1 to 2 weight percent of at least one emulsifying surfactant selected from the group consisting of polyoxyethylene sorbitan esters, polyoxyethylene fatty esters, alkyl phenoxy ethanols, fatty acid esters, alkanolamides and alkyl sulphates; and
   (d) 0.1 to 3 weight percent of a water-soluble polysaccharide.

25. A product as claimed in claim 24, wherein a mucoadhesive agent selected from the group consisting of sodium carboxymethylcellulose, polyacrylic acid, tragacanth, polyethylene oxide, sodium alginate, soluble starch, gelatin, pectin, polyvinyl pyrrolidone, polyethylene glycol and polyvinyl alcohol is present in an amount of 0.1 to 1.5 weight percent.

26. A product as claimed in claim 24, wherein the composition further comprises 0.001 to 25 weight percent of a pharmaceutically active substance.

27. A product as claimed in claim 26, wherein a mucoadhesive agent selected from the group consisting of sodium carboxymethylcellulose, polyacrylic acid, tragacanth, polyethylene oxide, sodium alginate, soluble starch, gelatin, pectin, polyvinyl pyrrolidone, polyethylene glycol and polyvinyl alcohol is present in an amount of 0.1 to 1.5 weight percent.

28. A product for rectal or vaginal administration, said product comprising a pressurised piston with can container containing an aqueous foamable composition having a delayed foaming action on expulsion from said pressurised container and a propellant separate therefrom for expelling said composition from the container, said composition comprising:
- (a) 65 to 95 weight percent of water;
- (b) 1.0 to 3.5 weight percent of foaming agent selected from the group consisting of propane, butane, iso-butane, pentane, 1,1,1,2,-tetrafluoro-ethane, 1,1,1,2,3,3,3,-heptafluoropropane, and mixtures thereof;
- (c) 0.1 to 2 weight percent of at least one emulsifying surfactant selected from the group consisting of polyoxyethylene sorbitan esters, polyoxyethylene fatty esters, alkyl phenoxy ethanols, fatty acid esters, alkanolamides and alkyl sulphates; and
- (d) 0.1 to 3 weight percent of a water-soluble polysaccharide.

29. A product as claimed in claim 28, wherein a mucoadhesive agent selected from the group consisting of sodium carboxymethylcellulose, polyacrylic acid, tragacanth, polyethylene oxide, sodium alginate, soluble starch, gelatin, pectin, polyvinyl pyrrolidone, polyethylene glycol and polyvinyl alcohol is present in an amount of 0.1 to 1.5 weight percent.

30. A product as claimed in claim 28, wherein the composition further comprises 0.001 to 25 weight percent of a pharmaceutically active substance.

31. A product as claimed in claim 30, wherein a mucoadhesive agent selected from the group consisting of sodium carboxymethylcellulose, polyacrylic acid, tragacanth, polyethylene oxide, sodium alginate, soluble starch, gelatin, pectin polyvinyl pyrrolidone, polyethylene glycol and polyvinyl alcohol is present in an amount of 0.1 to 1. 5 weight percent.

32. A product for rectal or vaginal administration, said product comprising a pressurised container containing an aqueous foamable composition having a delayed foaming action on expulsion from said pressurised container and a propellant separate therefrom for expelling said composition from the container, said composition comprising:
- (a) a major amount by weight of water,
- (b) a foaming agent in the form of a water-immiscible liquefied gas;
- (c) at least one emulsifying surfactant;
- (d) a water-soluble polymer; and
- (e) an effective amount of an anti-inflammatory agent selected from 4-aminosalicylic acid and 5-aminosalicylic acid.

33. A product as claimed in claim 32 wherein the pressurised container is a bag-in-can container.

34. A product as claimed in claim 32 wherein the pressurised container is a piston with can container.

35. A product as claimed in claim 2 wherein said composition comprises 57 to 97 weight percent of water.

36. A product as claimed in claim 32 wherein said composition comprises 57 to 97 weight percent of water.

37. A product as claimed in claim 35 wherein said composition comprises 65 to 95 weight percent of water.

38. A product as claimed in claim 36 wherein said composition comprises 65 to 95 weight percent of water.

39. A product as claimed in claim 2 comprising 0.5 to 7.0 weight percent of foaming agent.

40. A product as claimed in claim 32 comprising 0.5 to 7.0 weight percent of foaming agent.

41. A product as claimed in claim 39 comprising 1.0 to 3.5 weight percent of foaming agent.

42. A product as claimed in claim 40 comprising 1.0 to 3.5 weight percent of foaming agent.

43. A product as claimed in claim 41 wherein the foaming agent is selected from the group consisting of propane, butane, iso-butane, pentane, 1,1,1,2-tetrafluoroethane, 1,1,1,2,3,3,3-heptafluoropropane, and mixtures thereof.

44. A product as claimed in claim 42 wherein the foaming agent is selected from the group consisting of propane, butane, iso-butane, pentane, 1,1,1,2-tetrafluoroethane, 1,1,1,2,3,3,3-heptafluoropropane, and mixtures thereof.

45. A product as claimed in claim 2 containing 0.1 to 2 weight percent of emulsifying surfactant.

46. A product as claimed in claim 32 containing 0.1 to 2 weight percent of emulsifying surfactant.

47. A product as claimed in claim 45 wherein the emulsifying surfactant is selected from the group consisting of polyoxyethylene sorbitan esters, polyoxyethylene fatty esters, alkyl phenoxy ethanols, fatty acid esters, alkanolamides and alkyl sulphates.

48. A product as claimed in claim 46 wherein the emulsifying surfactant is selected from the group consisting of polyoxyethylene sorbitan esters, polyoxyethylene fatty esters, alkyl phenoxy ethanols, fatty acid esters, alkanolamides and alkyl sulphates.

49. A product as claimed in claim 41 wherein the emulsifying surfactant is a polyoxyethylene sorbitan ester.

50. A product as claimed in claim 48 wherein the emulsifying surfactant is a polyoxyethylene sorbitan ester.

51. A product as claimed in claim 2 containing 0.1 to 3 weight percent water-soluble polymer.

52. A product as claimed in claim 32 containing 0.1 to 3 weight percent water-soluble polymer.

53. A product as claimed in claim 51 wherein the water-soluble polymer is a water-soluble polysaccharide.

54. A product as claimed in claim 52 wherein the water-soluble polymer is a water-soluble polysaccharide.

55. A product as claimed in claim 53 wherein the polysaccharide is selected from the group consisting of xanthan gum, agar, guar gum, hydroxyethyl cellulose, hydroxypropyl cellulose, hydroxypropyl methylcellulose, and methyl cellulose.

56. A product as claimed in claim 54 wherein the polysaccharide is selected from the group consisting of xanthan gum, agar, guar gum, hydroxyethyl cellulose, hydroxypropyl cellulose, hydroxypropyl methylcellulose, and methyl cellulose.

57. A product as claimed in claim 55 wherein the water-soluble polymer is xanthan gum at 1 to 3% w/w.

58. A product as claimed in claim 56 wherein the water-soluble polymer is xanthan gum at 1 to 3% w/w.

59. A product as claimed in claim 2 wherein the active substance is present in an amount of 0.001 to 25 weight percent of the composition.

60. A product as claimed in claim 32 wherein the active substance is present in an amount of 0.001 to 25 weight percent of the composition.

61. A product as claimed in claim 2 wherein a mucoadhesive agent is present in an amount of 0.1 to 1.5 weight percent.

62. A product as claimed in claim 32 wherein a mucoadhesive agent is present in an amount of 0.1 to 1.5 weight percent.

63. A product as claimed in claim 61 wherein the mucoadhesive agent is selected from the group consisting of sodium carboxymethylcellulose, polyacrylic acid, tragacanth, polyethylene oxide, sodium alginate, soluble starch, gelatin, pectin, polyvinyl pyrrolidone., polyethylene glycol and polyvinyl alcohol.

64. A product as claimed in claim 62 wherein the mucoadhesive agent is selected from the group consisting of sodium carboxymethylcellulose, polyacrylic acid, tragacanth, polyethylene oxide, sodium alginate, soluble starch, gelatin, pectin, polyvinyl pyrrolidone, polyethylene glycol and polyvinyl alcohol.

65. A product as claimed in claim 63 wherein the mucoadhesive agent is carbomer.

66. A product as claimed in claim 64 wherein the mucoadhesive agent is carbomer.

67. A product composition as claimed in claim 2 having an expansion ratio of 10 to 20.

68. A product composition as claimed in claim 32 having an expansion ratio of 10 to 20.

* * * * *